United States Patent

Fomenko

[11] 4,070,114
[45] Jan. 24, 1978

[54] DETECTOR OPTICS FOR USE IN FABRIC INSPECTION

[75] Inventor: Sergei Michael Fomenko, Woodland Hills, Calif.

[73] Assignee: Greenwood Mills, Inc., Greenwood, S.C.

[21] Appl. No.: 662,955

[22] Filed: Mar. 1, 1976

[51] Int. Cl.² .................... G01B 9/02; G02B 27/38
[52] U.S. Cl. .................... 356/111; 250/550; 350/190
[58] Field of Search .......... 350/190, 204, 6; 250/550; 356/106 R, 111, 32

[56] References Cited

U.S. PATENT DOCUMENTS

| | | | |
|---|---|---|---|
| 3,664,739 | 5/1972 | Pryor | 356/32 |
| 3,762,793 | 10/1973 | Ullstig | 350/190 |
| 3,783,296 | 1/1974 | Blevins | 250/550 |
| 3,861,801 | 1/1975 | Peters et al. | 356/74 |
| 3,879,131 | 4/1975 | Cuthbert | 356/106 R |

*Primary Examiner*—Conrad J. Clark
*Attorney, Agent, or Firm*—Cushman, Darby & Cushman

[57] ABSTRACT

First and second pairs of mirrors are oriented to intercept first and second regions respectively of a diffraction pattern and deflect these regions to individual detectors so that simultaneous analysis of the regions of the diffraction pattern can be carried out. The pairs of mirrors can be spaced along the optical axis in a manner to provide focused regions of the diffraction pattern at the detectors wherein the diffraction pattern itself is imaged at two spaced focal planes resulting from astigmatic conditions. The physical arrangement not only overcomes problems introduced by astigmatism but also permits practical physical positioning of individual photo-diode arrays such that simultaneous processing of the regions in the diffraction pattern can be carried out.

7 Claims, 6 Drawing Figures

DETECTOR OPTICS FOR USE IN FABRIC INSPECTION

This invention relates generally to optical systems and more particularly to a detector optics system for analysis of a diffraction pattern developed from a coherent light beam used in inspecting materials such as fabrics manufactured in textile mills.

BACKGROUND OF THE INVENTION

Various materials such as fabric from textile mills will provide a diffraction pattern from a coherent light beam passed through the material characterized principally by a central lobe and first order side lobes. In the case of fabric wherein the cross sectional area of the coherent beam passing through the fabric encompasses a large number of warp and filling threads, the developed diffraction pattern in an output plane will include a central lobe and first order side lobes along first and second axes normal to the directions of the warp and filling respectively.

In copending U.S. patent application Ser. No. 660,252 filed Feb. 23, 1976 and entitled METHOD FOR AUTOMATIC FABRIC INSPECTION, assigned to the same assignee as the present invention, there is disclosed a basic method of fabric inspection by analysis of the diffraction pattern developed from passing a coherent light beam through fabric material. In accord with this method, the height and shapes of side lobes developed in various regions of the diffraction pattern are compared to given references representative of a "good" quality of fabric. A grade count can thus be assigned to any fabric being inspected.

In my copending U.S. patent application Ser. No 660,253 filed Feb. 23, 1976 and entitled COHERENT SCANNING SYSTEM FOR FABRIC INSPECTION, also assigned to the same assignee as the present invention, there is disclosed a scanning system enabling high speed automatic inspection of large fabric areas to be carried out by the method disclosed in the first mentioned copending application. Basically, this scanning system includes a scanning mirror which, through various optical components, causes the coherent beam to scan across the width of the fabric from one edge to the other. A de-scanning mirror has directed towards it the beam as it passes through successive areas across the width of the fabric, the de-scanning mirror then directing the coherent beam to appropriate detector optics. The beam, itself is at a slight angle in a vertical plane when reflected from appropriate concave mirrors towards the fabric, the de-scanning mirror being at a lower lever than the scanning mirror. Such off-axis reflections introduce astigmatism in the imaging of the final diffraction pattern.

More particularly, the astigmatic conditions result in imaging of the diffraction pattern in the vicinity of the de-scanning mirror in first and second focal planes spaced from each other, the various lobes themselves making up the diffraction pattern being elongated. Problems are thus introduced in attempting to employ conventional techniques in detecting and analyzing the diffraction pattern.

Another problem in the form of a practical consideration involves the general physical bulk of appropriate photo-diode linear detectors for analysis of a developed diffraction pattern. If it is desired to process various regions in the diffraction pattern which regions are spaced extremely close together, it is difficult if not impossible to place individual detectors in positions to enable simultaneous processing of the different regions.

In the analysis of the differential pattern developed in a high speed automatic fabric inspection system wherein scanning is employed such as described in the heretofore referred to copending patent applications, simultaneous analysis of various regions in each successively provided diffraction pattern would be of extreme benefit insofar as overall processing time is concerned.

BRIEF DESCRIPTION OF THE PRESENT INVENTION

Bearing the foregoing considerations in mind, the present invention contemplates the provision of a unique detector optics system particularly useful in conjunction with the analysis of diffraction patterns developed by scanning of fabric material wherein the foregoing problems of astigmatism and placement of bulky detectors are simultaneously solved.

Briefly, the detector optics enables simultaneously analyzing different regions in a diffraction pattern by utilizing in conjunction with at least two individual detectors, a first means positioned to intercept a first region of the diffraction pattern and direct it to one of the individual detectors, and a second means positioned to intercept a second region of the diffraction pattern and direct it towards another of the individual detectors. The arrangement enables convenient spaced positioning of the detectors so that the different regions can be processed simultaneously.

Where the diffraction pattern includes central and first order side lobes developed from a coherent light beam wherein astigmatic conditions result in an elongation of each lobe in a first direction in a first imaging plane and elongation of the lobes in a second direction normal to the first direction in a second imaging plane spaced a given distance from the first imaging plane along an optical axis of the beam, the referred to first means takes the form of a pair of mirrors positioned and oriented to intercept and reflect laterally first order side lobes in one region of the first imaging plane. The second means comprises a second pair of mirrors spaced from the first pair a distance constituting a function of the given distance along the optical axis separating the imaging planes as a consequence of astigmatism, the second pair of mirrors being oriented to intercept and reflect laterally the first order side lobes in another region of the second imaging plane. Cylindrical lenses in turn are positioned to receive the laterally deflected elongated lobe images respectively and squeeze them to remove the elongation and provide a focused lobe whereby the same may be readily detected and analyzed.

The separation of the imaging planes resulting from astigmatism is actually taken advantage of in that the respective regions in the imaging planes can readily be separated by the spaced pairs of mirrors so that ample room is provided for the photo-diode detector arrays, proper focusing on each of the arrays being assured.

BRIEF DESCRIPTION OF THE DRAWINGS

A better understanding of this invention will be had by now referring to the accompanying drawings in which.

DETAILED DESCRIPTION OF THE PREFERRED EMBODIMENT

Figure 1:
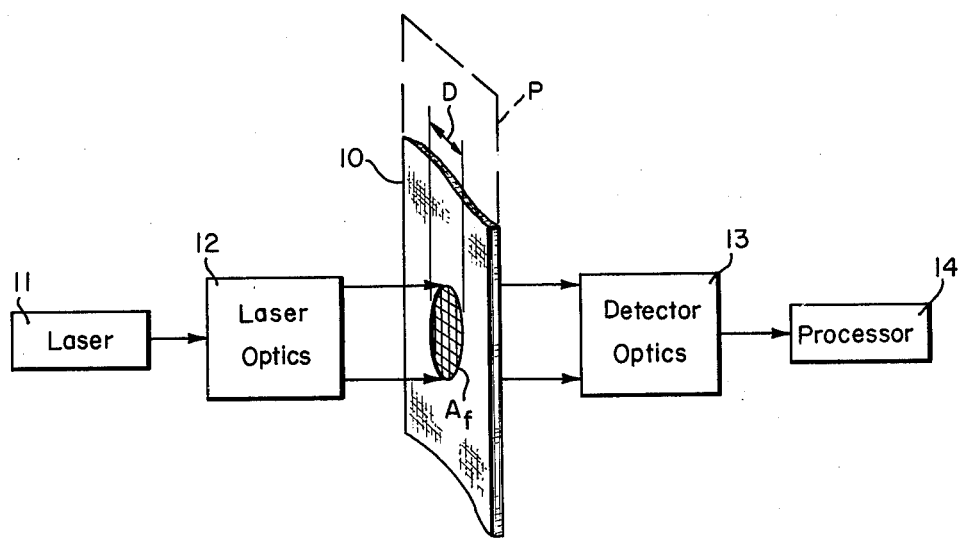
FIG. 1 is a simple schematic view of the basic components making up a fabric inspection system by analysis of a diffraction pattern.

Referring first to FIG. 1, there are shown basic components for enabling the investigation of a fabric material by diffraction pattern analysis. Thus, there is shown fabric 10 lying in a vertical plane P irradiated by a coherent beam from a laser 11 and appropriate laser optics 12. The beam diameter D is sufficient so that the area of fabric Af encompasses a relatively large number of warp and filling threads.

The warp and filling threads in the fabric generate a diffraction pattern which is detected on the other side of the fabric 10 by appropriate detector optics 13 from which the detected diffraction pattern passes to a processor 14 for analysis.

Normally, the diffraction pattern lies in a single focal output plane on the other side of the fabric 10 and for the material under consideration will take the form of a relatively large central lobe and first order side lobes.

Figure 2:
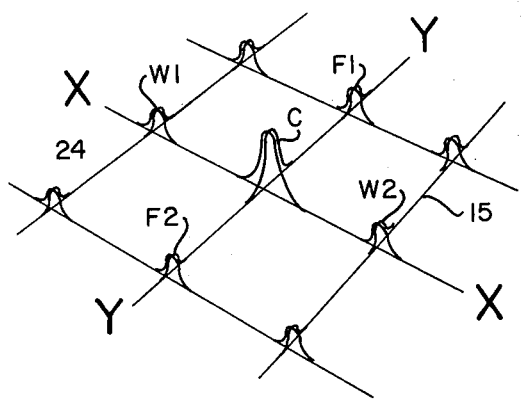
FIG. 2 is a diagrammatic representation of the diffraction pattern developed in a single focal plane by the system of FIG. 1.

FIG. 2 schematically depicts the output plane at 15 showing the relatively large central lobe C and various first order side lobes. The side lobes of importance lie along first and second axes Y—Y and X—X in the output plane 15 which axes are normal to the direction of the warp and filling threads respectively of the fabric 10. A pair of first order side lobes designated F1 and F2 on either side of the central lobe C fall on the first or Y—Y axis and represent regions wherein the diffraction pattern resulting from the filling threads in the fabric lie. The second or X—X axis in turn includes first order side lobes W1 and W2 on either side on the central lobe C in regions of the diffraction pattern resulting from the warp threads. In this respect, if the Y—Y axis is considered a vertical axis and the X—X axis a horizontal axis, the illustrated diffraction pattern develops when the warp of the fabric 10 of FIG. 1 run vertically and the filling horizontally. In other words, the first order side lobes F1 and F2 of FIG. 2 result from the horizontal filling of the fabric 10 and lie on a vertical axis Y—Y because of the diffraction of the light by the horizontal threads in an up and down direction. Similarly, the first order side lobes W1 and W2 result from the diffraction of the light by the vertical warp of the fabric 10 which diffract the coherent light to the left and right as viewed in the drawings.

It is desirable to simultaneously analyze different regions of the diffraction pattern such as those occupied by the side lobes W1 and W2 distinct from those regions in which the side lobes F1 and F2 occur. However, it is not convenient to detect these regions separately in view of the relatively large physical bulk of the detectors involved and the small distances between the lobes in the pattern.

Figure 3:
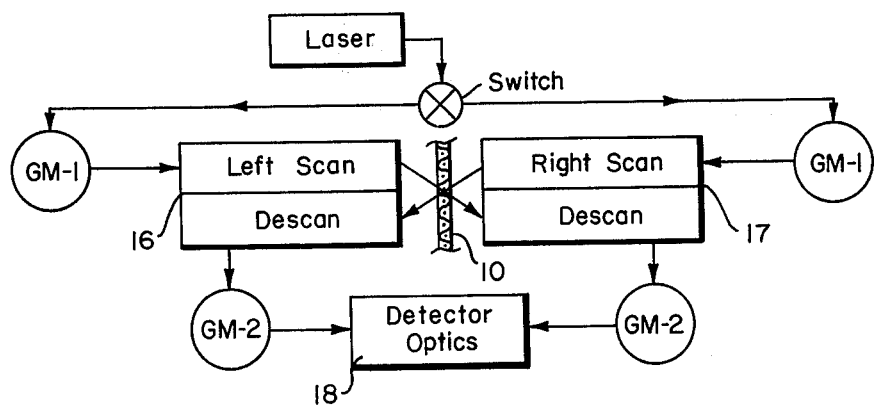
FIG. 3 is a block diagram of a scanning system for inspecting fabric which by necessity introduces astigmatism in the diffraction pattern.

Referring now to FIG. 3 there is shown in block form a scanning system for investigating the fabric 10 of FIG. 1 along the lines described in the second of the above-mentioned copending applications. In accord with these teachings, there is provided a laser and appropriate beam switch for diverting the coherent light beam alternately to scanning mirrors GM-1 to the left of the fabric and GM-1 to the right of the fabric. The moving light beam from each of the scanning mirrors passes through left and right scan portions of left and right housings 16 and 17 and are respectively de-scanned by appropriate de-scanning optics in these housings including de-scanning mirrors GM-2 at the left to descan radiation from the right scan and GM-2 at the right for de-scanning radiation from the left scan.

As mentioned earlier, the provision of the scanning and de-scanning at different levels results in astigmatism being introduced into the diffraction pattern images occurring in the vicinity of the de-scanning mirrors GM-2. This astigmatism has two effects on the diffraction pattern: first, the central and side lobes are all elongated in a first direction in a first imaging plane. Second, a second imaging plane of the diffraction pattern is created spaced a given distance from the first imaging plane and also imaging elongated lobes in which the direction of elongation is at right angles or normal to the direction of elongation in the first imaging plane.

Figure 4:
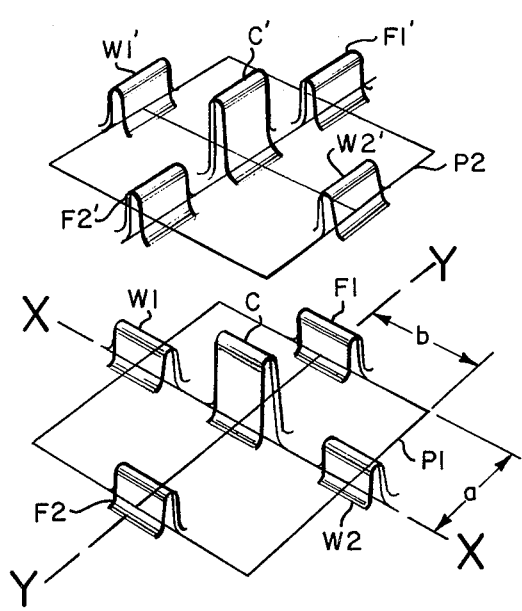
FIG. 4 is highly diagrammatic representation of first and second imaging planes of the diffraction pattern of FIG. 2 illustrating elongated central and side lobes resulting from the referred to astigmatism.

FIG. 4 diagramatically illustrates these first and second imaging planes at P1 and P2.

Thus rather than the diffraction pattern illustrated in FIG. 2, the diffraction pattern resulting from astigmatic conditions causes elongation of the central and side lobes in one direction, for example, the direction of the X—X axis in the first imaging plane P1 and, elongation of the central and side lobes indicated by the same letters followed by $a'$ in a direction normal to the X—X direction; that is, along the Y—Y axis in the second imaging plane P2.

The diffraction pattern in one of the planes, for example, the plane P2 would occur at the de-scanning mirror GM-2, the other spaced diffraction pattern having a virtual imaging behind the de-scanning mirror.

As mentioned earlier, the detector optics system of the present invention not only enables simultaneous and independent analysis of the warp side lobes and filling side lobes but also permits accommodation of relatively bulky photo-diode linear arrays to be properly positioned in spite of the relatively close spacing of the lobes and the double imaging thereof resulting from astigmatism.

Figure 5:
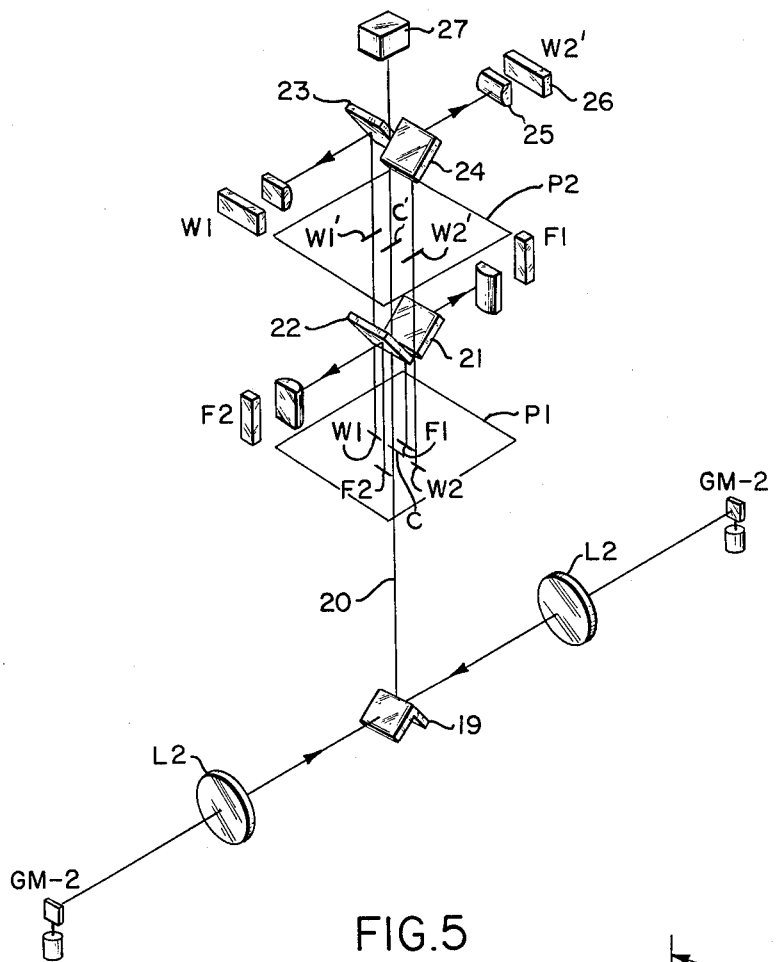
FIG. 5 is a schematic illustration of the basic components making up the detector optics for analysis of the diffraction pattern in the imaging planes shown in FIG. 4; and, FIG. 6 is an enlarged perspective view of certain ones of the components in the detector system of FIG. 5.

FIG. 5 schematically depicts these detector optics designed for cooperation with the scanning system of FIG. 3. Thus, referring to FIG. 5, the coherent beams alternately passing from the de-scanning mirrors GM-2 pass through appropriate relay lenses L2 to a combining mirror means 19 to provide a beam passing vertically upwardly along optical axis 20. The imaging of the elongated lobes in spaced first and second imaging planes P1 and P2 in accord with the patterns described in FIG. 4 is reproduced in FIG. 5 by short line segments identified with the same letters to distinguish the filling lobes from the warp lobes.

It should be understood that the scanning apparatus of FIG. 3 giving rise to astigmatic conditions is merely one example. In other situations, any optical transform means receiving the initial diffraction pattern and imaging the same could have astigmatic conditions resulting in imaging in first and second spaced imaging planes and elongation of the lobes as described.

Still referring to FIG. 5, there are provided in accord with the present invention, a first pair of spaced mirrors 21 and 22 oriented at 45° to and on opposite sides of the optical axis 20 of the beam. These mirrors are in positions to thus receive and reflect laterally the imaged side lobes in the first imaging plane along the first axis. These particular side lobes are the F1 and F2 lobes described in FIG. 4, shown along the V—V axis, and reproduced in the plane P1 of FIG. 5. The central lobe C and the warp side lobes W1' and W2' in the second imaging plane P2 pass between the first pair of mirrors 21 and 22 because of their spacing on either side of the V—V axis.

A second pair of spaced mirrors 23 and 24 lying in planes oriented at 45° to and on opposite sides of the optical axis 20 of the beam are positioned to receive and reflect laterally the imaged side lobes in the second imaging plane P2 along the second axis.

Four individual cylindrical lenses are positioned to receive the laterally reflected side lobes from the four mirrors making up the first and second pairs respectively. Each cylindrical lens functions to squeeze its received elongated side lobe image in a direction to remove its elongation and provide a focused lobe. Co-operating with the cylindrical lenses are four individual linear photo-diode arrays positioned to receive the focused lobes respectively and provide substantially simultaneously, individual output signals constituting functions of the intensity distribution and positions of the lobes.

Except for the orientation, the various cylindrical lenses and photo-diode linear detectors are the same and therefore a further description of one will suffice for all.

By way of example, in FIG. 5 the side lobe W2' reflected by the mirror 24 in the second pair passes through a cylindrical lens 25 to squeeze the lobe in the direction of its elongation into a focused lobe at the photo-diode linear detector 26. The other lobes F1, F2 and W1' are similarly squeezed and detected by corresponding cylindrical lenses and detectors. The spacing between the mirrors in each pair is such that the lobes C and C' both pass between all of the mirrors to a photo-detector 27.

Figure 6:
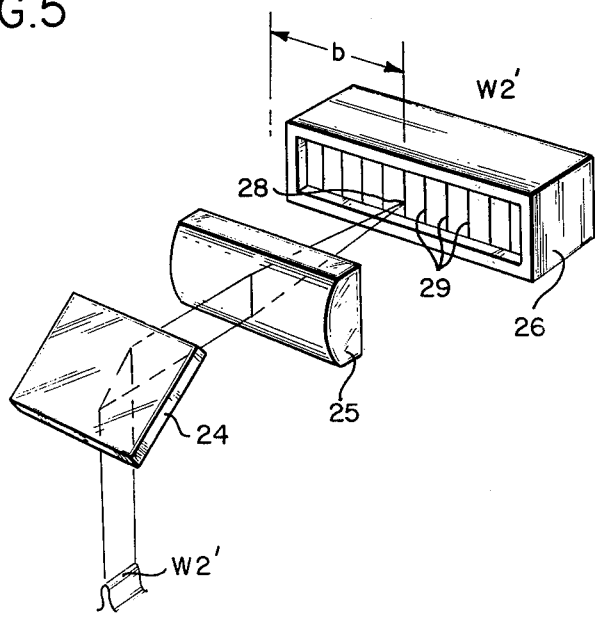

FIG. 6 shows the reflecting mirror 24, cylindrical lens 25 and detector 26 in greater detail wherein it will be noted that the focused lobe occurs at diode 28 to be accommodated within the linear photo-diode array. This array consists of a row of photo-diodes 29 which detect the varying intensities and positions of the light within the focused lobe. It will be understood that there are many more photo-diodes provided in the array than indicated by the vertical lines 29 in FIG. 6, the latter simply being schematic.

The focused lobe actually is spread in a linear manner along the row of diodes, the intensity of light increasing and then decreasing in accord with the amplitude envelope of the lobe. In the example shown, maximum intensity occurs about in the center of the array on diode 28. By correlating the position of this point of maximum intensity with the position of the central lobe, that is the centroid spacing or distance to the Y—Y axis as indicated as $b$ in plane P1 of FIG. 4, information is provided as to the distance between the centroids of the various side lobes. The corresponding distance $b$ from a reference point adjacent to one end of the array is indicated in FIG. 6. This distance is indicative of the warp threads per inch.

The intensity distribution of light within the focused lobe, on the other hand, will be determined by signals developed from adjacent diodes encompassed within the focused lobe in the array.

In the system described, advantage is actually taken of the provision of first and second imaging planes resulting from astigmatism. The fact that these imaging planes are spaced from each other along the optical axis allows a physical separation of the second pair of mirrors from the first pair of mirrors and yet permits proper focusing of the various side lobes onto their associated photo-detectors. Thus, the given distance between the first and second imaging planes P1 and P2 of FIG. 4 will determine the physical distance between the first pair of mirrors 21, 22 and second pair of mirrors 23, 24 along the optical axis 20 of the beam in FIG. 5. Because of normally provided intermediate optics, such as the lens L2, the physical spacing between the pairs of mirrors will constitute a function of the given spacing between the imaging planes in the vicinity of the de-scanning mirrors GM-2. For example, the distance between the mirrors might be greater by five or six times the distance between the actual imaged planes at GM-2.

This spacing, as noted heretofore, is taken advantage of in that it is a very simple matter to properly position the photo-diode linear detectors to receive the reflected side lobes even though the detectors are relatively bulky and of large size.

In FIG. 5, the imaging planes P1 and P2 are shown below the respective pairs of mirrors for convenience. Actually, the elongated lobe imaging would be very close to the mirrors.

As mentioned heretofore, the central lobe images C and C' pass directly to the detector 27. Primarily, the detector 27 will simply measure the intensity of the light lobe and is not concerned with the intensity distribution. The effect of both center lobes C and C', which actually are one lobe imaged in different planes, is simply integrated in detector 27.

The detector optics of this invention accordingly resolves both the problems of astigmatic conditions and physical accommodation of detectors all to the end that the various different regions of a developed diffraction pattern can be individually analyzed substantially simultaneously.

It should be understood in the specific example given in FIG. 5 that the combining mirrors 19 could be eliminated and only the coherent beam from one of the de-scanning mirrors GM-2 passed directly to the spaced pairs of mirrors, a duplicate set of spaced mirrors, cylindrical lenses and detectors being provided for the other beam from the other de-scanning mirror GM-2. However, by using the combining mirror means 19 the same detectors can be used for the alternately provided coherent beams from each of the de-scanning mirrors.

Further, while the preferred embodiment has described various optical components as constituting mirrors, optical elements performing equivalent functions such as lenses or prisms could be used. For example, the functions of the pairs of spaced mirrors could be carried out by any optical means which would appropriately direct the lobe images to the detectors. Also, the function of the cylindrical lens could be performed by any other type of optical squeezing means.

What is claimed is:

1. A detector optics system for receiving and processing at least one side lobe region in a diffraction pattern developed from a coherent light beam wherein astigmatic conditions result in an elongation of at least one lobe in said region in an imaging plane, comprising:

optical means for intercepting and directing the image of at least said one elongated lobe in said one region of said imaging plane, and optical squeezing means positioned to receive each so directed elongated lobe image and to squeeze same for removing the elongation and providing a focused lobe which may be readily detected and analyzed.

2. A detector optics system for independently processing substantially simultaneously at least first order side lobes of a diffraction pattern developed from a coherent light beam, comprising:

four separate light detectors, imaging means for splitting said beam to develop four separate images respectively of four different first order side lobes, and four optical squeezing means respectively positioned to receive said four lobe images for squeezing and focusing the lobe images respectively onto said separate light detectors substantially simultaneously.

3. A detector optics system for analyzing a diffraction pattern developed by a light beam in which astigmatic conditions result in the imaging of the pattern in first and second planes spaced along the optical axis of the beam including:

first analyzing means including first intercept means positioned to intercept a first region of the diffraction pattern image in said first plane for analyzing the intercepted image, and second analyzing means including second inercept means spaced from said first intercept means along said optical axis and positioned to intercept a second region of the diffraction pattern image in said second plane for analyzing the second region intercepted image, the spacing of said second intercept means from said first intercept means being determined by the spacing between said first and second planes.

4. A detector optics system for receiving and independently processing substantially simultaneously at least first order side lobe regions in a diffraction pattern developed from a coherent light beam wherein astigmatic conditions result in an elongation of each lobe in a first direction in a first imaging plane and elongation of the lobes in a second direction normal to the first direction in a second imaging plane spaced a given distance from the first imaging plane along the axis of the beam, including, in combination:

a. first optical means for intercepting and directing the elongated images of first order side lobes in one region of said first imaging plane;

b. second optical means spaced from said first optical means a distance constituting a function of said given distance along said optical axis and oriented to intercept and direct the elongated images of the first order side lobes in another region of said second imaging plane, and c. optical squeezing means positioned to receive the directed elongated lobe images respectively and squeeze them to remove the elongation and provide a focused lobe which may be readily detected and analyzed.

5. In a fabric inspection apparatus wherein a diffraction pattern is developed in an output plane from a single coherent light beam passing through a large number of warp and fill threads making up the fabric, a detector optics system for receiving and independently processing central and first order side lobes in said diffraction pattern lying along first and second axes in said output plane normal to the warp and filling respectively, including:

a. optical transform means for receiving said diffraction pattern and imaging said central and side lobes wherein astigmatic conditions result in an elongation of each lobe in a first direction in a first imaging plane and elongation of the lobes in a second direction normal to the first direction in a second imaging plane spaced a given distance from the first imaging plane along the optical axis of the beam;

b. a first pair of spaced mirrors oriented at a given angle to and on opposite sides of the optical axis of said beam in positions to receive and reflect laterally the side lobes along said first axis imaged in said first imaging plane;

c. a second pair of spaced mirrors lying in planes oriented at a given angle to and on opposite sides of the optical axis of said beam in positions to receive and reflect laterally side lobes along said second axis imaged in said second imaging plane;

d. four individual optical squeezing means positioned to receive the laterally reflected side lobes from the four mirrors making up the first and second pairs respectively, each optical squeezing means squeezing its received elongated side lobe image in a direction to remove its elongation and provide a focused lobe; and e. four individual linear photo-diode arrays positioned to receive the focused side lobes respectively and provide substantially simultaneously individual output signals constituting functions of the intensity distribution and positions of the lobes.

6. A system according to claim 5, in which the spacing between the two mirrors of each pair is sufficient to pass the central lobe of said diffraction pattern and wherein there is provided a photo-detector beyond said second pair of spaced mirrors for receiving said central lobe and in which said first and second pairs of mirrors are physically spaced along the optical axis of the beam by a distance constituting a function of said given distance to optimize the proper focusing of side lobes in the first and second imaging planes on the associated linear photo-diode arrays, respectively whereby signal information for the central lobe and individual signal information for each of the side lobes can all be individually analyzed substantially simultaneously.

7. A system according to claim 5, in which said given angle of orientation of the first and second pairs of mirrors is 45° and in which each of said optical squeezing means comprises a cylindrical lens.

* * * * *